(12) United States Patent
Cao et al.

(10) Patent No.: US 12,153,031 B1
(45) Date of Patent: Nov. 26, 2024

(54) DETECTION DEVICE AND METHOD OF RARE GAS SAMPLE IN FORMATION WATER

(71) Applicant: Northwest Institute of Eco-Environment and Resources, CAS, Lanzhou (CN)

(72) Inventors: Chunhui Cao, Lanzhou (CN); Liwu Li, Lanzhou (CN); Zhifu Wei, Lanzhou (CN); Zhongping Li, Lanzhou (CN); Lantian Xing, Lanzhou (CN); Yan Liu, Lanzhou (CN)

( * ) Notice: Subject to any disclaimer, the term of this patent is extended or adjusted under 35 U.S.C. 154(b) by 0 days.

(21) Appl. No.: 18/791,353

(22) Filed: Jul. 31, 2024

(30) Foreign Application Priority Data

Nov. 27, 2023 (CN) .......................... 202311592297.0

(51) Int. Cl.
  *G01N 33/00* (2006.01)
  *G01N 33/18* (2006.01)
(52) U.S. Cl.
  CPC ......... *G01N 33/0027* (2013.01); *G01N 33/18* (2013.01)
(58) Field of Classification Search
  CPC .............. G01N 33/18; G01N 33/0027; G01N 33/0036; E21B 43/281; B01D 53/26

USPC .............................................. 73/864.35, 31.05
See application file for complete search history.

(56) References Cited

U.S. PATENT DOCUMENTS

2024/0044862 A1* 2/2024 Pujol .................. G01N 33/2823

FOREIGN PATENT DOCUMENTS

JP          4007542 B2 * 11/2007

* cited by examiner

*Primary Examiner* — John Fitzgerald
*Assistant Examiner* — Truong D Phan (57) ABSTRACT

A detection device includes a chamber, a top of the chamber is cover with a chamber cover, and a side wall of the chamber is provided with a port D5. The chamber is provided with a first waterproof layer and a second waterproof layer, and a water storage layer is disposed between the first waterproof layer and the second waterproof layer. A water supply pipe is disposed in the water storage layer, and the water supply pipe includes a port D2 and a port D7. An end second pipe is connected to the port D2, and another end of the second pipe facing away from the first pipe is provided with a port D3. An online detection component and a vacuum extraction system are disposed outside the chamber. The detection device can quantitatively simulate and detect the process of rare gas migration and accumulation under formation water conditions.

5 Claims, 5 Drawing Sheets

DETECTION DEVICE AND METHOD OF RARE GAS SAMPLE IN FORMATION WATER

TECHNICAL FIELD

The disclosure relates to the technical field of rare gas detection device, and particularly to a detection device and method of a rare gas sample in formation water.

BACKGROUND

Oxygen and nitrogen are the most abundant and common gas components in groundwater systems, typically accounting for 1% to 4% of the volume of groundwater. Carbon dioxide is the most important gas component in terms of chemical and regulatory properties in the groundwater, with significant variations in content across different groundwater systems. The general concentration range in water bodies is about 10 milligrams per liter (mg/L) to 50 mg/L, but in some areas, the content of carbon dioxide in groundwater can even exceed 1000 mg/L. Groundwater also contains other gas components, such as methane and helium. The content and types of these gas components vary depending on the region, geological conditions, and human activities.

The rare gases in the groundwater have scientific application value. For example, helium, as an important strategic resource, is an essential raw material in high-tech fields such as semiconductors, superconductivity, and aerospace. Detecting components and content of the rare gases in groundwater is of great significance for studying the migration and accumulation processes of the rare gases in groundwater.

The detection device in the related art is to detect the composition of gases in water under current strata conditions, such as Chinese patents with publication No. CN102128859B and CN116482308B. However, it is well known to those skilled in the art that the composition of rare gases in groundwater varies with different strata conditions. Additionally, due to the differences in detection methods for gas sample and the gas components in formation water, existing gas collection and detection devices cannot be directly used to detect the gas component in the formation water. To study the migration and accumulation processes of rare gases in groundwater, it is necessary to investigate the composition of rare gases under different formation water conditions. Currently, there is no experimental device that can simulate and detect the migration and accumulation processes of rare gases under formation water conditions.

SUMMARY

To "simulate and detect the migration and aggregation process of rare gases in formation water conditions", the disclosure provides a detection device and method of rare a gas sample in formation water.

The detection device of rare gas samples in formation water is provided. The detection device includes a chamber, the chamber defines a space, and a top of the chamber is provided with a chamber cover covering the chamber. The chamber is provided with a first waterproof layer and a second waterproof layer, and a water storage layer is disposed between the first waterproof layer and the second waterproof layer to separate the first waterproof layer and the second waterproof layer. A side wall of the chamber located at the first waterproof layer is connected to a port D8, and the side wall of the chamber located at the second waterproof layer is connected to a port D5. A gap is defined between the first waterproof layer and each of corresponding inner walls of the chamber, and a gap is defined between the second waterproof layer and each of corresponding inner walls of the chamber. A water supply pipe extends through the water storage layer, and the water supply pipe includes a port D2 and a port D7. The chamber and the water storage layer are defined with pairs of perforations, and the water supply pipe penetrates the pairs of perforations. The port D7 is disposed inside the water storage layer, and the port D2 is disposed outside the chamber. A first pipe is connected to the port D2, and an end of a second pipe is connected to the first pipeline. Another end of the second pipe is a port D3, and the port D3 is connected to a dehydrator. The online detection component and the vacuum extraction system are both detachably connected to at least one selected from the group consisting of the dehydrator, the port D5 and the port D8 through connection pipes, and valves are disposed on each of the connection pipes.

In an embodiment, materials of the first waterproof layer and the second waterproof layer both are standard rock cores; or, a material of the second waterproof layer is a standard rock core, and a material of the first waterproof layer is a mixture of soil and sand.

In an embodiment, the water storage layer includes a supporting housing, and a top of the supporting housing and a bottom of the supporting housing defines openings, respectively. A bottom of the first waterproof layer is disposed on an inner bottom surface of the chamber, the support housing is disposed above a top of the first waterproof layer, and the top of the first waterproof layer is adjacent to the opening at the bottom of the support housing. The second waterproof layer is disposed at the opening at the top of the support housing, and the water storage layer is in a sealed state.

In an embodiment, a water storage component is disposed outside the chamber, the water storage component is connected to an end of the first pipe, and another end of the first pipe is provided with a port D1. The port D1 is detachably connected to the port D2, the first pipe can be connected to the water supply pipe, and a valve V1 is disposed on the first pipe. The first pipe is connected to an end of the second pipe at a position of the first pipe between the valve V1 and the port D1, and another end of the second pipe facing away from the first pipe is provided with port D3.

In an embodiment, the online detection component is provided with an inlet port, and a four-way component is connected to the inlet port, an end of a third pipe, an end of a fourth pipe, and an end of a fifth pipe. Another end of the third pipe is provided with a port D4, and the port D4 is detachably connected to the port D3. A valve V2 is disposed on the third pipe, another end of the fourth pipe is provided with a port D6, the port D6 is detachably connected to the port D5 and the port D8 through a three-way component, and a valve V3 is disposed on the fourth pipe. Another end of the fifth pipe is connected to the vacuum extraction system, and a valve V4 is disposed on the fifth pipe. A valve V6 is disposed between the port D5 and the chamber, and a valve V7 is disposed between the port D8 and the chamber.

In an embodiment, the first pipe is provided with a first thermometer and a first pressure gauge thereon, and the water storage layer is provided with a second thermometer and a second pressure gauge therein.

In an embodiment, a drying component is disposed between the chamber and the valve V6, that is, a side wall of the chamber connected to the port D5 is provided with the drying component, the drying component includes an installation housing, a fixed drying component and a movable drying component, the installation housing includes a side wall, and the side wall defines an upstream opening and a downstream opening, the upstream opening is disposed close to the chamber and a downstream opening is disposed close to the valve V6. The fixed drying component is fixedly disposed inside the installation housing and is disposed to seal the upstream opening of the installation housing, and the movable drying component is disposed at the downstream opening of the installation housing and to be capable of moving. An end of the fixed drying component close to the downstream opening of the installation housing is provided with a connecting rod, a center position of the movable drying component defines a sleeving hole, the movable drying component is movably sleeved on the connecting rod, and the movable drying component is configured to rotate around an axial direction of the connecting rod.

In an embodiment, the fixed drying component is cylindrical, and a cylindrical outer side surface of the fixed drying component is in contact with an inner wall of the installation housing. The fixed drying component includes a frame, a desiccant is provided inside the frame, and the frame is provided with inclined first ventilation ducts.

In an embodiment, the dehydrator is disposed on the third pipe and is disposed between the port D4 and the valve V2. The dehydrator includes a water storage area, a heating area, and a drying area, the water storage area is connected to the third pipe and is disposed close to the port D4, the drying area is connected to the third pipe and is disposed close to the valve V2, and the water storage area is disposed above the heating area.

In an embodiment, a method for detecting the rare gas samples in the formation water includes steps as follows.

The steps includes:

assembling the detection device;

turning on the vacuum extraction system to vacuumize the detection device except for a water storage component;

injecting the formation water into the water storage layer, injecting formation water into the dehydrator to make the dehydrator absorb water molecules of the formation water to thereby obtain gas in the formation water as the rare gas sample and make the gas in the formation water enter the online detection component, and detecting a gas component content of the gas by the online detection component;

after detecting the component content of the gas, injecting formation water into the water storage layer under pressure until a target pressure value is reached, and followed by heating the formation water in the water storage layer to a target temperature value;

monitoring a component content of gas flowing out of the first waterproof layer by the online detection component, and recording a corresponding pressure value and a corresponding temperature value of the first waterproof layer; and monitoring the component content of gas flowing out of the second waterproof layer by the online detection component, and recording a corresponding pressure value and a corresponding temperature value of the second waterproof layer;

where the corresponding component content of gas flowing out of each of the first waterproof layer and the second waterproof layer is monitored by the online detection component until the corresponding component content of gas no longer changes.

The beneficial effects of the disclosure are as follows.

The formation water commonly understood in a narrow sense refers to confined water, which is bounded by aquicludes above and below. Based on the distribution patterns of the formation water, the disclosure provides a detection device and a method of a rare gas sample in formation water. The water chamber is designed for injecting the formation water, the formation water can be actual groundwater collected from the field or simulated groundwater with components that mimic natural groundwater, containing rare gases. The first waterproof layer and the second waterproof layer are configured to prevent the water from permeating, which is preferred to use materials that simulate formation conditions. When the pressure and temperature in the water chamber change, the rare gases permeate and migrate through the gap between the first waterproof layer and each of corresponding inner walls of the chamber, and the gap between the second waterproof layer and each of corresponding inner walls of the chamber. The component content of the rare gases also changes. By measuring the component content of the permeated and migrated rare gases, one can quantitatively simulate the permeation and aggregation processes of the rare gases in the formation water under different conditions, such as temperature and pressure.

In the disclosure, the purpose of the fixed drying component and the movable drying component is to adsorb water molecules and dry the gas. The drying components are used to absorb the water molecules that permeate, allowing only the gas components to enter the online detection component, thus avoiding damage to the online detection component from water molecules and reducing the detection load on the online detection component. The structure of the dehydrator in the disclosure is simple and easy to operate.

DETAILED DESCRIPTION OF EMBODIMENTS

In order to enable those skilled in the art to better understand the technical solution of the disclosure and implement it, the disclosure will be further explained in conjunction with specific embodiments and attached drawings.

In the description of the disclosure, it should be understood that terms such as "center," "longitudinal," "lateral," "length," "width," "thickness," "top," "bottom," "front," "back," "left," "right," "vertical," "horizontal," "top," "bottom," "inside," "outside," "clockwise," "counterclockwise," "axial," "radial," and "circumferential" refer to the orientation or positional relationships based on the orientation or positions shown in the attached drawings. These terms are used solely for the purpose of describing the disclosure and simplifying the description, and do not indicate or imply that the devices or components referred to must have a specific orientation, be constructed and operated in a specific orientation. Therefore, they should not be construed as limitations of the disclosure.

The terms "first" and "second" are used only for descriptive purposes and should not be construed as indicating or implying relative importance or suggesting the number of the technical features being referred to. Thereby, features specified with "first" or "second" may explicitly or implicitly include one or more of such features. In the description of the disclosure, unless otherwise specified, the term "multiple" means two or more.

Figure 1:
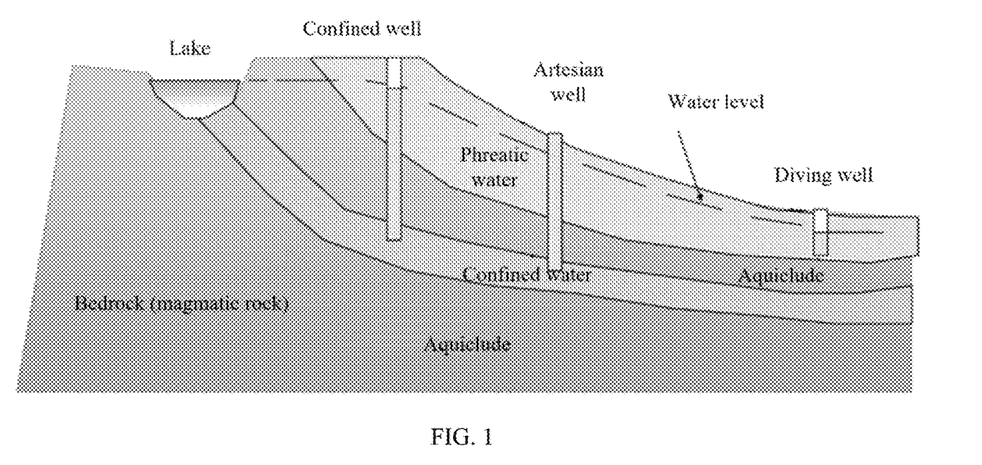
FIG. 1 illustrates a distribution of formation water in the disclosure.

As shown in FIG. 1, the general distribution pattern of formation water is as follows: from top to bottom, it includes the phreatic area, aquitard, confined water, and the bedrock layer, and the bedrock layer is also an aquitard. The formation water commonly understood in a narrow sense refers to the confined water, which is bounded by aquitards above and below. Based on these distribution patterns of the formation water, the disclosure provides a detection device of rare gas samples in formation water and a detection method therefor, including the following embodiments.

Embodiment 1

Figure 2:
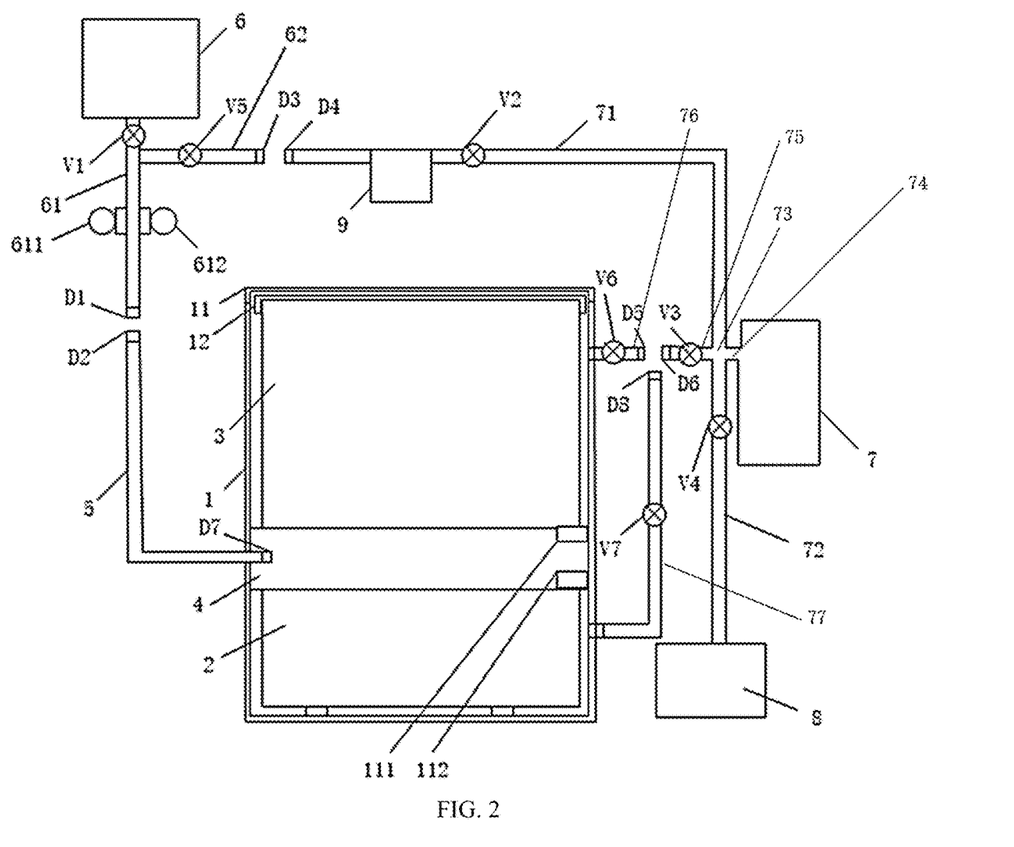
FIG. 2 illustrates a schematic structural diagram of a detection device of a rare gas sample in formation water according to an embodiment 1 of the disclosure.

A detection device of a rare gas sample in formation water is provided, as shown in FIGS. 1-2, the detection device includes a chamber 1, the chamber 1 defines a space, and a top of the chamber 1 is provided with a chamber cover 11 covering the chamber 1, and the chamber 1 and the chamber cover 11 can be detachably connected through screw connection or flange connection. A first waterproof layer 2 and a second waterproof layer 3 are disposed the space of the chamber 1, a water storage layer 4 is disposed between the first waterproof layer 2 and the second waterproof layer 3, the water storage layer 4 is configured to be injected with the formation water, and the formation water can be collected groundwater from actual scenes or simulated groundwater components prepared, containing rare gases. The water storage layer 4 is configured to separate the first waterproof layer 2 and the second waterproof layer 3. A gap is defined between the first waterproof layer 2 and each of corresponding inner walls the chamber 1, and a gap is defined between the second waterproof layer 3 and each of corresponding inner walls of the chamber 1. The chamber 1 is provided with a sixth pipe 76 at a side wall of the second waterproof layer 3, an end of the sixth pipe 76 facing away from the chamber 1 is provided with a port D5, the port D5 is configured to communicate the inside and outside of chamber 1, and the gap between the second waterproof layer 3 and the corresponding inner wall of the chamber 1 is connected to the port D5. The sixth pipe 76 is provided with a valve V6 between the port D5 and chamber 1, and a side wall of the chamber 1 located at the first waterproof layer 2 is provided with a seventh pipe 77. An end of the seventh pipe 77 facing away from the chamber 1 is provided with a port D8, the port D8 is configured to communicate the inside and outside of chamber 1, the gap the first waterproof layer 2 and the corresponding inner wall of the chamber 1 is connected to the port D8, and the seventh pipe 77 is provided with a valve V7 between the port D8 and the chamber 1. The first waterproof layer 2 and the second waterproof layer 3 are configured to block water. In an embodiment, both of the first waterproof layer 2 and the second waterproof layer 3 are made of materials that simulate formation conditions, for example, standard cores are used for both the first waterproof layer 2 and the second waterproof layer 3. Specifically, a diameter of the cylindrical standard core is 25 millimeters (mm) or 38 mm, and a length of less than 300 mm. The chamber 1 is also cylindrical, and a central axis of both the first waterproof layer 2 and the second waterproof layer 3 coincide with the central axis of the chamber 1; or, a length of the standard rectangular cores is in a range of 1-1200 mm; or a material of the second waterproof layer 3 may use a standard core, and a material of the first waterproof layer 2 may be a mixture of soil and sand. Exemplarily, when using materials such as the mixture of soil and sand with a particle size less than or equal to 0.5 centimeters (cm), a filter plate 31 is disposed above the water storage layer 4 in the chamber 1. Then, the materials such as the mixture of soil and sand with a particle size less than or equal to 0.5 cm are placed on the filter plate 31. The filter plate 31 defines filter holes with a diameter smaller than the particle size of the material of the second waterproof layer 3. For example, when the particle size of the material of the second waterproof layer 3 is between 0.1-0.5 cm, the diameter of the filter holes is set in a range of 0.01-0.05 cm.

Figure 3:
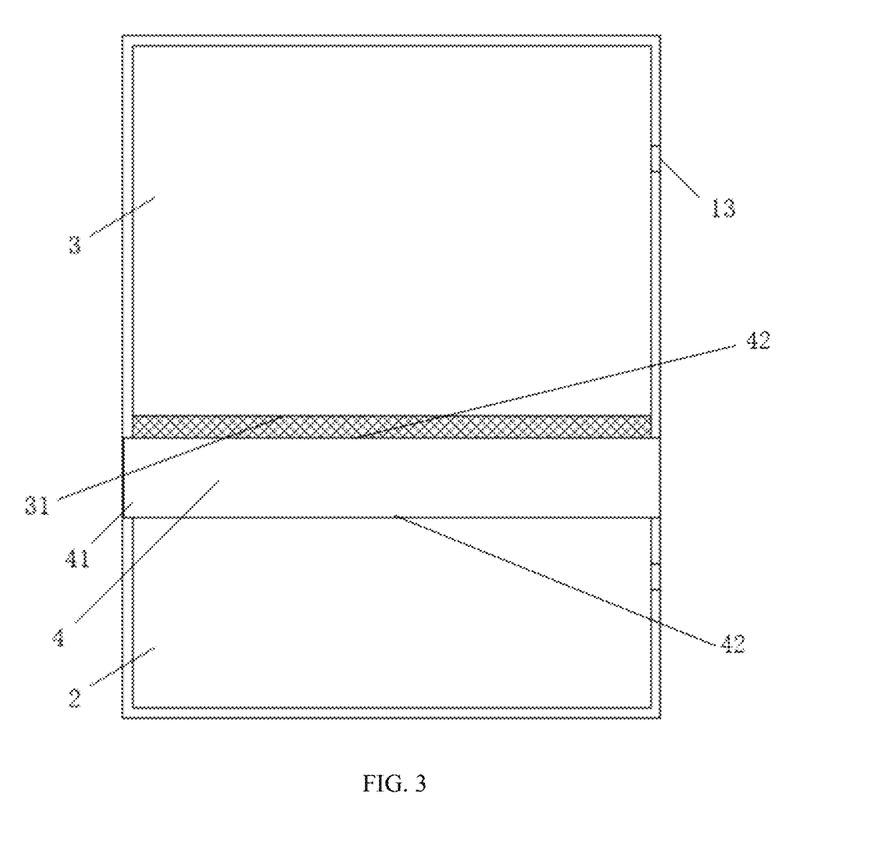
FIG. 3 illustrates a longitudinal sectional view of a chamber and its internal structure according to the embodiment 1 of the disclosure.

A water supply pipe 5 extends through the water storage layer 4, and the water supply pipe 5 includes a port D2 and a port D7. The water storage layer 4 includes a supporting housing 41, a top of the supporting housing 41 and a bottom of the supporting housing 41 defines openings (42), respectively, and side walls of the supporting housing 41 are in a sealed state. A bottom of the first waterproof layer 2 is disposed on an inner bottom surface of the chamber 1, the support housing 41 is disposed above a top of the first waterproof layer 2, and the top of the first waterproof layer 2 is adjacent to the opening at the bottom of the support housing 41. The second waterproof layer 3 is disposed at the opening at the top of the support housing 41, and the water storage layer 4 is in a sealed state. To enhance the sealing performance, after the chamber cover 11 is connected to the top of the chamber 1, a seam between the chamber 1 and the chamber cover 11 is sealed with a sealing glue. A sealing lid 12 is disposed inside the chamber cover 11, there is. After the sealing lid 12 is connected to the top of the second waterproof layer 3, the seam between the sealing lid 12 and the second waterproof layer 3 is also sealed with the sealing glue. The side walls of the chamber 1 and the side walls of the water storage layer 4 are defined with pairs of perforations. The water supply pipe 5 is disposed to penetrate the pairs of perforations, with the port D7 disposed inside the water storage layer 4 and the port D2 disposed outside the chamber 1. To further improve the sealing performance, the connection between the water supply pipe 5 and the chamber 1 is also sealed with sealing glue.

In an embodiment, an outer wall of the port D7 is provided with a heating device, such as a heating plate, heater, or heating jacket. The heating device is used to heat the water in the water storage layer 4 to simulate different temperatures of the formation water.

The formation water is delivered into the water storage layer 4 through the water supply pipe 5, and then the formation water permeates and migrates into the gap between the first waterproof layer 2 and the corresponding inner wall of chamber 1, as well as the gap between the second waterproof layer 3 and the corresponding inner wall of chamber 1. Even if water molecules cannot completely pass through the first waterproof layer 2 and the second waterproof layer 3, the rare gases in the formation water still permeate and migrate through the gap between the first waterproof layer 2 and the corresponding inner wall of chamber 1, and the gap between the second waterproof layer 3 and the corresponding inner wall of chamber 1. When there are changes in pressure and temperature within the water storage layer 4, the component content of the rare gases that permeate and migrate into the gap between the first waterproof layer 2 and the corresponding inner wall of chamber 1, and the gap between the second waterproof layer 3 and the corresponding inner wall of chamber 1, also changes. By measuring the component content of the permeated and migrated rare gases, it is possible to quantitatively simulate the permeation and aggregation processes of the rare gases in formation water under different conditions, such as temperature and pressure.

As shown in FIG. 1, a water storage component 6 is disposed outside the chamber 1, the water storage component 6 is connected to an end of the first pipe 61, and another end of the first pipe 61 is provided with a port D1. The port D1 is detachably connected to the port D2, and the first pipe 61 is communicated with the water supply pipe 5. A valve V1 is disposed on the first pipe 61, the valve V1 is used to control whether formation water flows through or not. The first pipe 61 is connected to an end of the second pipe 62 at a position of the first pipe 61 between the valve V1 and the port D1, and another end of the second pipe 62 facing away from the first pipe 61 is provided with a port D3, and a valve V5 is disposed on the second pipe 62.

An online detection component 7 and a vacuum extraction system 8 are disposed outside the chamber 1. The online detection component 7 is configured to detect the component content of rare gases, such as existing technology gas detectors, gas component analyzers, and similar device. The online detection component 7 is provided with an inlet port 74, and a four-way component 73 is connected to the inlet port 74. The four-way component 73 is provided with a first end, a second end, a third end, and a fourth end on each way, respectively. The first end is connected to and communicated with the air inlet of the online detection component 7, with the connection seam sealed by the sealing glue. The second end is connected to an end of the third pipe 71, the third end is connected to an end of the fourth pipe, and the fourth end is connected to an end of the fifth pipe 72. Another end of the third pipe 72 is provided with port D4, which is detachably connected to the port D3, and a valve V2 is disposed on the third pipe 71. Another end of the fourth pipe is provided with port D6, which is detachably connected to the port D5 and the port D8 through a three-way component, and a valve V3 is disposed on the fourth pipe. Another end of the fifth pipe 72 is connected to the vacuum extraction system 8, which is a vacuum pump or other equipment with vacuuming capabilities, and a valve V4 is disposed on the fifth pipe 72. The third pipe 71 is provided with the dehydrator 9 between the port D4 and the valve V2, the dehydrator 9 is designed to intercept formation water, allowing only gases to pass through the valve V2. For example, the dehydrator 9 may be a drying device or a gas-liquid separator.

It should be noted that the overall device of the disclosure needs to maintain a low leak rate for the rare gases. The main body should be made of 304 stainless steel with electrolytic polishing, and the valves V1-V7 should be the all-metal ultra-high vacuum valves from the VAT Company. The corresponding ports D1-D8 should be connected with high vacuum flange connections. The online detection component 7 uses a quadrupole mass spectrometer from Pfeiffer Vacuum.

The first pipe 61 is provided with a first thermometer 611 and a first pressure gauge 612 thereon. The first thermometer 611 is used to measure the temperature of the water inside the first pipe 61, and the first pressure gauge 612 is used to measure the pressure of the water inside the first pipe 61. A second thermometer 111 and a second pressure gauge 112 are disposed inside the water storage layer 4 therein, the second thermometer 111 is used to measure the temperature of the water inside the water storage layer 4, and the second pressure gauge 112 is used to measure the pressure of the water inside the water storage layer 4.

The method for analyzing the permeation and migration characteristics of the rare gases in formation water using the detection device of this embodiment includes steps as follows.

1. The detection device is assembled based on the above structure. For example, the chamber 1 defines a space, and a top of the chamber 1 is covered with a chamber cover 11. The water storage layer 4 includes a supporting housing 41, the supporting housing 41 is disposed on a top of the first waterproof layer 2, and the top of the first waterproof layer 2 is adjacent to the opening at the bottom of the support housing 41. The second waterproof layer 3 is disposed at the opening at the top of the support housing 41, which makes the water storage layer 4 be in a sealed state, thereby enhancing the sealing performance. The water storage component 6 is connected to the first pipe 61, and the inlet port 74 of the online detection component 7 is connected to a four-way component 73. The first end is connected to and communicated with the air inlet of the online detection component 7, the second end is connected to an end of the third pipe 71, the third end is connected to an end of the fourth pipe, and the fourth end is connected to an end of the fifth pipe 72. Another end of the third pipe 72 is provided with port D4, and a valve V2 is disposed on the third pipe 71. Another end of the fourth pipe is provided with port D6, and a valve V3 is disposed on the fourth pipe. Another end of the fifth pipe 72 is connected to the vacuum extraction system 8. In addition, the corresponding connection joints are sealed with the sealing glue.

2. The port D1 and the port D2 are connected, the port D3 and the port D4 are connected, and the port D5, the port D8 and the port D6 are connected.

3. The water storage component 6 is configured to contain the formation water, the formation water can be actual groundwater collected from the field or artificially prepared to simulate the composition of groundwater. The water contains rare gases, such as helium, neon, argon, krypton, xenon, and so on.

4. The vacuum extraction system is turned on, the valve V1 is closed, and the valve V2, the valve V3, the valve V4, the valve V5, the valve V6 and the valve V7 are open.

5. When the readings of the first pressure gauge 612 and the second pressure gauge 112 are both below $10^{-6}$ pascals (Pa), the valves V2, V3, V4, V6, and V7 are closed.

6. The valves V1 and V2 are opened to allow the water to be delivered into the water storage layer 4 through the first pipe 61 and the water supply pipe 5. At the same time, the valve V5 is open for a period, such as one minute, thereby to inject a certain amount of the water into the dehydrator 9. After the dehydrator 9 absorbs the water molecules of the water, gas in the formation water is obtained as the rare gas sample, the valve V2 is opened to let the gas enter the online detection component 7. This gas contains rare gases. By using the online detection component 7 to detect the component content of the gas in the water storage layer 4, the component content of rare gases in the water can be quantified. It should be noted that the valve V2 can be opened at the same time as the valve V5, or the valve V5 can be opened for a period first, and then valve V2 can be opened.

7. After the detection of the component content of the gas is completed, the valves V2 and V5 are closed. The formation water is pressurized and delivered into the water storage layer 4. When the reading on the first pressure gauge 612 reaches the targeted pressure value, the valve V1 is closed. This step uses the first pressure gauge 612 to display the pressure of the water delivered into the water storage layer 4, which can be set to different pressure values according to experimental requirements.

8. The heating device is turned on to maintain the reading on the first thermometer 611 at the targeted temperature value. This step uses the first thermometer 611 to display the temperature of the water delivered into the water storage layer 4, which can be set to different temperature values according to detection requirements.

9. The valves V3 and V6 are opened, the online detection component 7 monitors the component content of the gas seeping from the first waterproof layer 2 inside the chamber 1 in real time and records the values of the first thermometer 611 and the second thermometer 111, and the first pressure gauge 612 and the second pressure gauge 112 in real time. When the readings of the first pressure gauge 612 and the second pressure gauge 112 are equal, and the component content of the gas seeping out, as monitored by the online detection component 7, no longer changes, the detection the gas in the first waterproof layer 2 is concluded.

10. The valve V6 are closed, and the valve V7 are opened. The online detection component 7 monitors the component content of the gas seeping from the second waterproof layer 3 inside the chamber 1 in real time and records the values of the first thermometer 611 and the second thermometer 111, and the first pressure gauge 612 and the second pressure gauge 112 in real time. When the readings of the first pressure gauge 612 and the second pressure gauge 112 are equal, and the component content of the gas seeping out, as monitored by the online detection component 7, no longer changes, the detection the gas in the second waterproof layer 3 is concluded.

11. Based on experimental data such as the duration of the experiment, the permeation amount of each gas component within the same period, rock porosity (i.e., permeability), temperature, and pressure, one can obtain the seepage characteristics of helium in helium-rich natural gas under different environmental conditions. This allows for the study of the migration and accumulation processes of helium under actual geological conditions.

Embodiment 2

Figure 4:
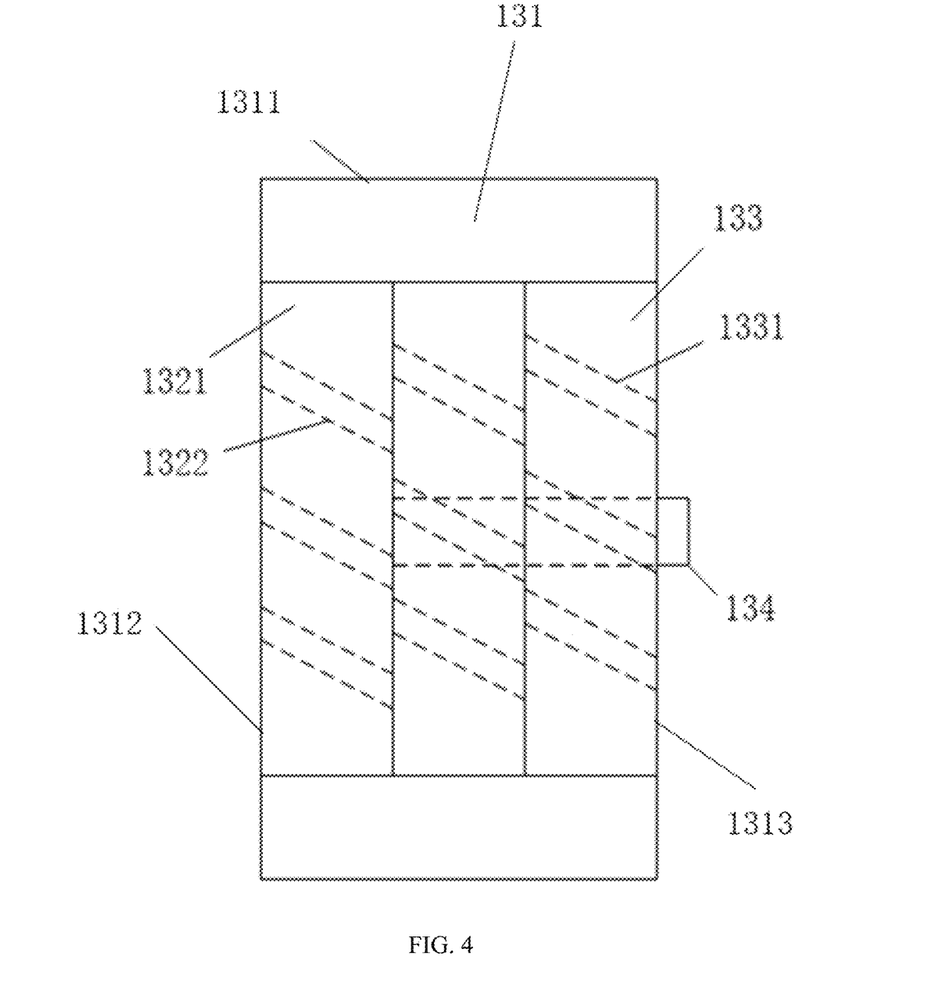
FIG. 4 illustrates a longitudinal sectional view of a drying component according to an embodiment 2 of the disclosure.

A detection device of a rare gas sample in formation water is provided, and the structure of the detection device is basically the same as the embodiment 1, except that a side wall of the chamber 1 connected to the port D5 is provided with the drying component 13.

Figure 5:
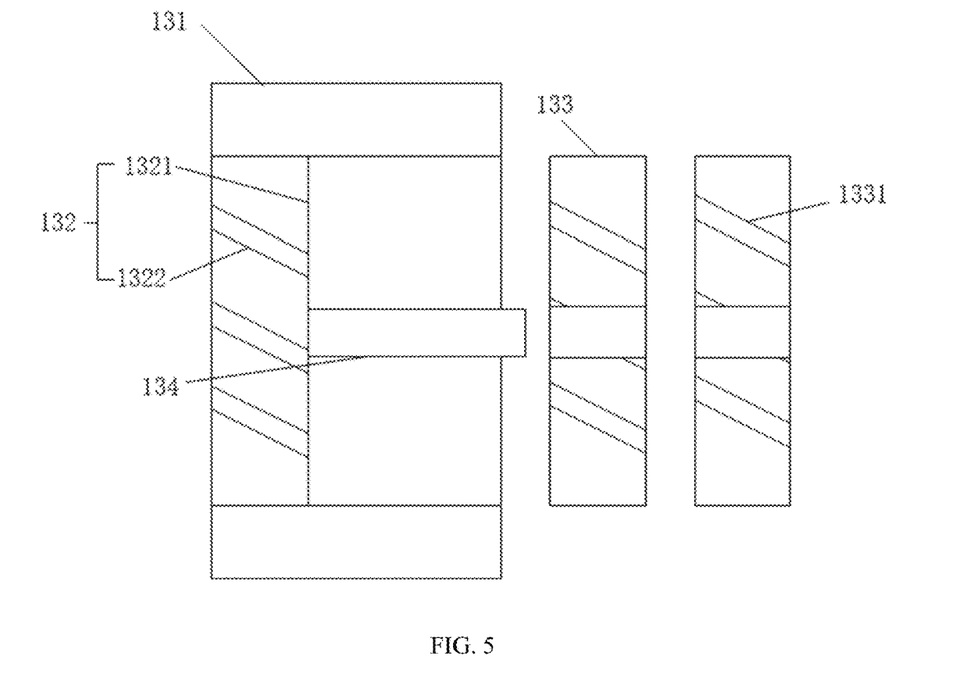
FIG. 5 illustrates an explosive view of the drying component according to the embodiment 2 of the disclosure.

As shown in FIGS. 3-5, the drying component 13 includes an installation housing 131, a fixed drying component 132 and a movable drying component 133, the installation housing 131 includes a side wall, and the side wall of the installation housing 131 defines an upstream opening 1312 close to the chamber 1 and a downstream opening 1313 close to the port D5. Preferably, the side walls are sealed side walls. The fixed drying component 132 is fixedly disposed inside the installation housing 131 and is disposed to seal the upstream opening 1312 of the installation housing 131, and the movable drying component 133 is disposed inside the installation housing 131 to be movable. An end of the fixed drying component 132 close to the downstream opening 1313 of the installation housing 131 is provided with a connecting rod 134 fixedly connected to the end of the fixed drying component 132, a center position of the movable drying component 133 defines a sleeving hole, the movable drying component 133 is movably sleeved on the connecting rod 134, and the movable drying component 133 is configured to rotate around an axial direction of the connecting rod 134. The functions of both the fixed drying component 132 and the movable drying component 133 is to adsorb water molecules and dry the gas. The drying components 13 are used to absorb the water molecules that permeate, allowing only the gas components to enter the online detection component 7. This prevents damage to the online detection component 7 from water molecules and reduces the detection load on the online detection component 7.

In an embodiment, the fixed drying component 132 is cylindrical, a cylindrical outer side surface of the fixed drying component 132 is in contact with an inner wall of the installation housing 131, and the sealing glue is used at the joint between the fixed drying component 132 and the inner wall of the installation housing 131. The fixed drying component 132 includes a frame 1321, a desiccant is provided inside the frame 1321, and the frame 1321 is provided with inclined first ventilation ducts 1322. The first ventilation ducts 1322 can be provided with the desiccant or not. When the desiccant is in powder or granular form, such as anhydrous sodium sulfate or calcium chloride, it should be wrapped in a breathable material bag. Care should be taken to use a desiccant made of material that does not absorb gas molecules or absorbs gas molecules with difficulty, to avoid interfering with the experimental results.

Figure 6:
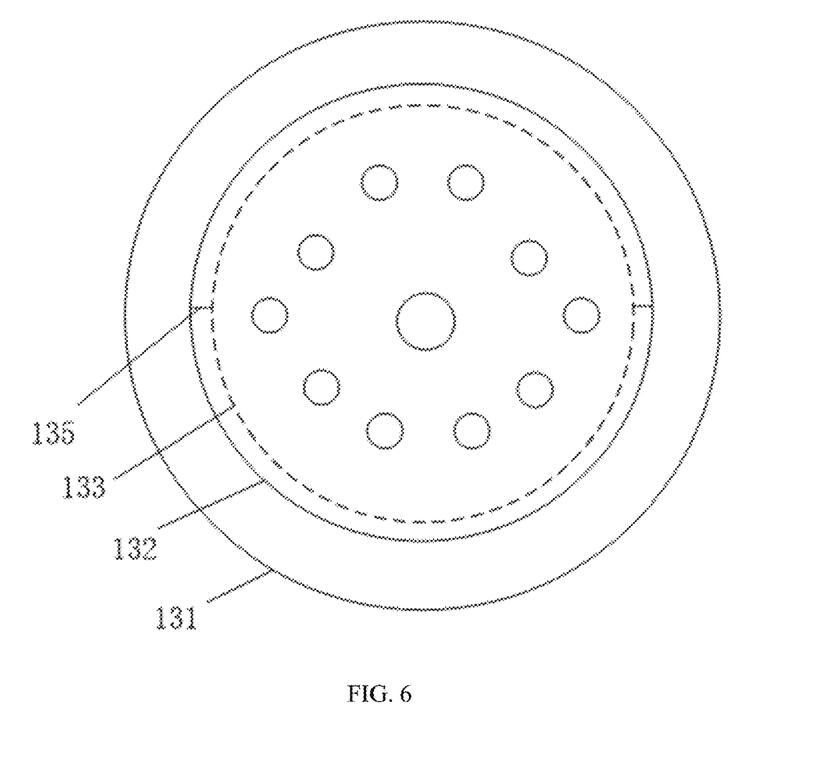
FIG. 6 illustrates a transverse sectional view of the drying component according to the embodiment 2 of the disclosure.

In an embodiment, the movable drying component 133 is cylindrical, and a diameter of the movable drying component 133 is smaller than a diameter of the inner wall of the installation housing 131. A connecting component 135 is disposed between the outer wall of the movable drying component 133 and the inner wall of the installation housing 131. For example, the connecting component 135 is an elastic rope or an elastic band. When the permeated gas passes through the inclined first ventilation ducts 1322 of the fixed drying component 132, the expelled air is also inclined. Additionally, since the movable drying component 133 is rotatably connected to the connecting rod 134, the inclined air blows the movable drying component 133 to rotate. The connecting component 135 pulls on the movable drying component 133, restricting its excessive rotation. This structure of the drying component 13 can reduce the velocity of the gas entering the fourth pipe, allowing it to enter the online detection component 7 gently for the detection. It also reduces the impact of the gas on the connections of the port D5 and the port D6, preventing gas leaks.

In an embodiment, an interior of the movable drying component 133 defines second ventilation ducts 1331. When the movable drying component 133 is initially installed onto the connecting rod 134, the first ventilation ducts 1322 and the second ventilation ducts 1331 are arranged to intersect. After the inclined air blows and rotates the movable drying component 133, the first ventilation ducts 1322 and the second ventilation ducts 1331 can be connected for a period of time. This allows the drying component 13 to dry and slow down the gas. As a result, the airflow can be relatively stable, which is conducive to the precise analysis of component content of the gas by the online detection component 7.

Embodiment 3

Figure 7:
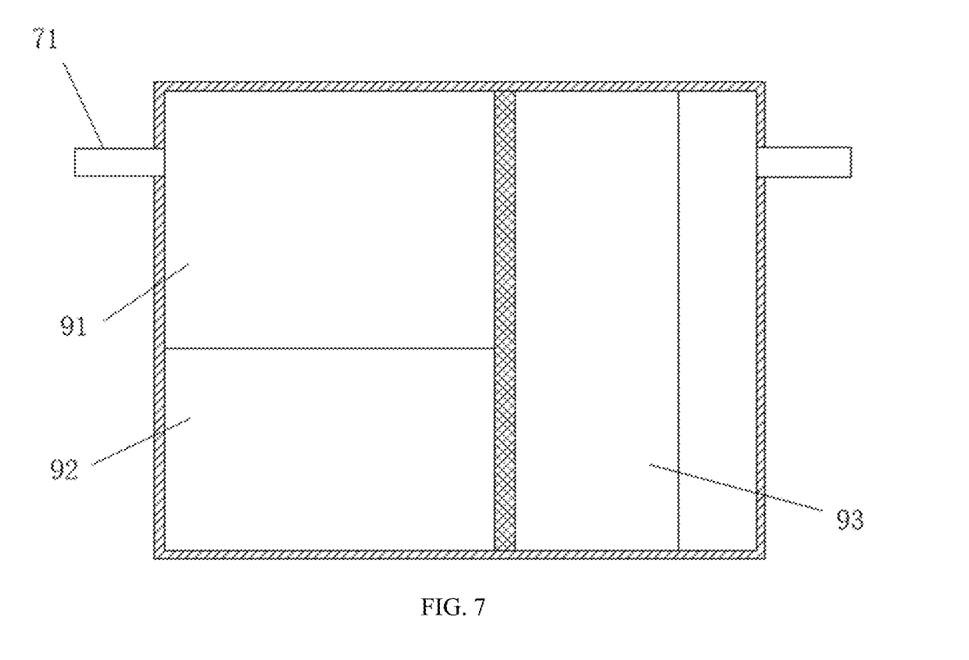
FIG. 7 illustrates a longitudinal sectional view of a dehydrator according to an embodiment 3 of the disclosure.

A detection device of a rare gas sample in formation water is provided, and the structure of the detection device is basically the same as the embodiment 1, except that a dehydrator is shown in FIG. 7. The dehydrator 9 includes a water storage area 91, a heating area 92, and a drying area 93. An end of the third pipe 71 close to the port D4 is connected to the water storage area 91, another end of the third pipe 71 close to the valve V2 is connected to the drying area 93, the water storage area 91 is disposed above the heating area 92, and the drying area 93 is disposed on the same sides of the water storage area 91 and the heating area 92. Preferably, the drying area 93 and the heating area 92, as well as the drying area 93 and the water storage area 91, are both separated by fixed plates, with the two fixed plates stacked and bonded to each other. An upper end of the fixed plate between the drying area 93 and the water storage area 91 defines air holes, which facilitates the passage of gas or water vapor. Note that the height of the formation water added to the water storage area 91 should be lower than the height of the air holes. The water from the port D4 first enters the water storage area 91, then is heated and evaporated towards the drying area 93 through the heating area 92. The drying area 93 absorbs water molecules, and the remaining gas enters the online detection component 7 for analysis.

In addition, the heating area 92 is provided with a heating plate or other components that have heating functions, and the drying area 93 includes a desiccant.

It should be noted that in the disclosure, the connection relationships of components not specifically mentioned are, by default, made using the related art. Since they do not involve the creative points and are widely applied in the related art, the structural connection relationships are not described in detail.

It should be noted that when the disclosure involves numerical ranges, each endpoint of the range and any number within the range should be understood as being selectable. Since the steps and methods used are the same as those in the embodiment, to avoid redundancy, the disclosure describes preferred embodiments. Although the preferred embodiments of the disclosure have been described, those skilled in the art, once they are aware of the basic creative concept, can make other changes and modifications to these embodiments. Therefore, the appended claims are intended to be interpreted as including the preferred embodiments and all changes and modifications that fall within the scope of the disclosure.

Apparently, those skilled in the art can make various modifications and variations to the disclosure without departing from the spirit and scope of the disclosure. Thus, if these modifications and variations of the disclosure fall within the scope of the claims and their equivalents, the disclosure is intended to include such modifications and variations as well.

What is claimed is:

1. A detection device of a rare gas sample in formation water, the detection device comprising:
   a chamber (1), wherein a top of the chamber (1) is provided with a chamber cover (11) covering the chamber (1), and an online detection component (7) and a vacuum extraction system (8) are disposed outside the chamber (1);
   wherein the chamber (1) is provided with a first waterproof layer (2), a water storage layer (4), and a second waterproof layer (3) sequentially arranged in that order from bottom to top; a gap is defined between the first waterproof layer (2) and each of corresponding inner walls of the chamber (1), and a gap is defined between the second waterproof layer (3) and each of corresponding inner walls of the chamber (1); a side wall of the chamber (1) located at the first waterproof layer (2) is connected to a port D8, and the side wall of the chamber (1) located at the second waterproof layer (3) is connected to a port D5; a water supply pipe (5) extends through the water storage layer (4), and the water supply pipe (5) comprises a port D2 and a port D7; and the water supply pipe (5) penetrates the chamber (1) and the water storage layer (4), the port D7 is disposed inside the water storage layer (4), and the port D2 is disposed outside the chamber (1);
   wherein a water storage component (6) is disposed outside the chamber (1), the water storage component (6) is connected to an end of a first pipe (61), and another end of the first pipe (61) is provided with a port D1; the port D1 is detachably connected to the port D2, and a valve V1 is disposed on the first pipe (61); the first pipe (61) is connected to an end of the second pipe (62) at a position of the first pipe (61) between the valve V1 and the port D1; another end of the second pipe (62) is provided with a port D3, and the port D3 is connected to a dehydrator (9);
   wherein the first pipe (61) is provided with a first thermometer (611) and a first pressure gauge (612) thereon, and the water storage layer (4) is provided with a second thermometer (111) and a second pressure gauge (112) therein;
   wherein a valve V6 is disposed between the chamber (1) and the port D5, a drying component (13) is disposed between the chamber (1) and the valve V6, the drying component (13) comprises an installation housing (131), a fixed drying component (132) and a movable drying component (133), the installation housing (131) comprises a side wall (1311), and the side wall defines an upstream opening (1312) and a downstream opening (1313), the upstream opening (1312) is disposed close to the chamber (1) and the downstream opening (1313) is disposed close to the valve V6; the fixed drying component (132) is fixedly disposed inside the installation housing (131) and is disposed to seal the upstream opening (1312) of the installation housing (131), and the movable drying component (133) is disposed at the downstream opening (1313) of the installation housing (131); and an end of the fixed drying component (132) close to the downstream opening (1313) of the installation housing (131) is provided with a connecting rod (134), the movable drying component (133) is movably sleeved on the connecting rod (134), and the movable drying component (133) is configured to rotate around an axial direction of the connecting rod (134);
   wherein the online detection component (7) is provided with an inlet port (74), and a four-way component (73) is connected to the inlet port (74), an end of a third pipe (71), an end of a fourth pipe (75), and an end of a fifth pipe (72); another end of the third pipe (71) is provided with a port D4, and the port D4 is detachably connected to the port D3; a valve V2 is disposed on the third pipe (71), another end of the fourth pipe (75) is provided with a port D6, the port D6 is detachably connected to the port D5 and the port D8, and a valve V3 is disposed on the fourth pipe (75); another end of the fifth pipe (72) is connected to the vacuum extraction system (8), and a valve V4 is disposed on the fifth pipe (72); a valve V6 is disposed between the port D5 and the chamber (1), and a valve V7 is disposed between the port D8 and the chamber (1); and wherein the dehydrator (9) is disposed on the third pipe (71) and is disposed between the port D4 and the valve V2; the dehydrator (9) comprises a water storage area (91), a heating area (92), and a drying area (93); the water storage area (91) is connected to the third pipe (71) and is disposed close to the port D4, the drying area (93) is connected to the third pipe (71) and is disposed close to the valve V2, and the water storage area (91) is disposed above the heating area (92).

2. The detection device of the rare gas sample in formation water as claimed in claim 1, wherein materials of the first waterproof layer (2) and the second waterproof layer (3) both are standard rock cores; or,
a material of the second waterproof layer (3) is a standard rock core, and a material of the first waterproof layer (2) is a mixture of soil and sand.

3. The detection device of the rare gas sample in formation water as claimed in claim 2,
wherein the water storage layer (4) comprises a supporting housing (41), and a top of the supporting housing (41) and a bottom of the supporting housing (41) defines openings (42), respectively; a bottom of the first waterproof layer (2) is disposed on an inner bottom surface of the chamber (1), the support housing (41) is disposed above a top of the first waterproof layer (2); and the top of the first waterproof layer (2) is adjacent to the opening at the bottom of the support housing (41), the second waterproof layer (3) is disposed at the opening at the top of the support housing (41), and the water storage layer (4) is in a sealed state.

4. The detection device of the rare gas sample in formation water as claimed in claim 1, wherein the fixed drying component (132) is cylindrical, and a cylindrical outer side surface of the fixed drying component (132) is in contact with an inner wall of the installation housing (131); and the fixed drying component (132) comprises a frame (1321), a desiccant is provided inside the frame (1321), and the frame (1321) is provided with inclined first ventilation ducts (1322) thereon.

5. A method for detecting the rare gas sample in formation water, adopted for the detection device as claimed in claim 1, comprising:

assembling the detection device;

turning on the vacuum extraction system (8) to vacuumize the detection device except for the water storage component (6);

injecting formation water into the water storage layer (4), injecting formation water into the dehydrator (9) to make the dehydrator (9) absorb water molecules of the formation water to thereby obtain gas in the formation water as the rare gas sample and make the gas in the formation water enter the online detection component (7), and detecting a component content of the gas by the online detection component (7);

after detecting the component content of the gas, injecting formation water into the water storage layer (4) under pressure until a target pressure value is reached, and followed by heating the formation water in the water storage layer (4) to a target temperature value;

monitoring a component content of gas flowing out of the first waterproof layer (2) by the online detection component (7), and recording a corresponding pressure value and a corresponding temperature value of the first waterproof layer (2); and monitoring a component content of gas flowing out of the second waterproof layer (3) by the online detection component (7), and recording a corresponding pressure value and a corresponding temperature value of the second waterproof layer (3);

wherein the corresponding component content of gas flowing out of each of the first waterproof layer (2) and the second waterproof layer (3) is monitored by the online detection component (7) until the corresponding component content of gas no longer changes.

* * * * *